Figure 1:
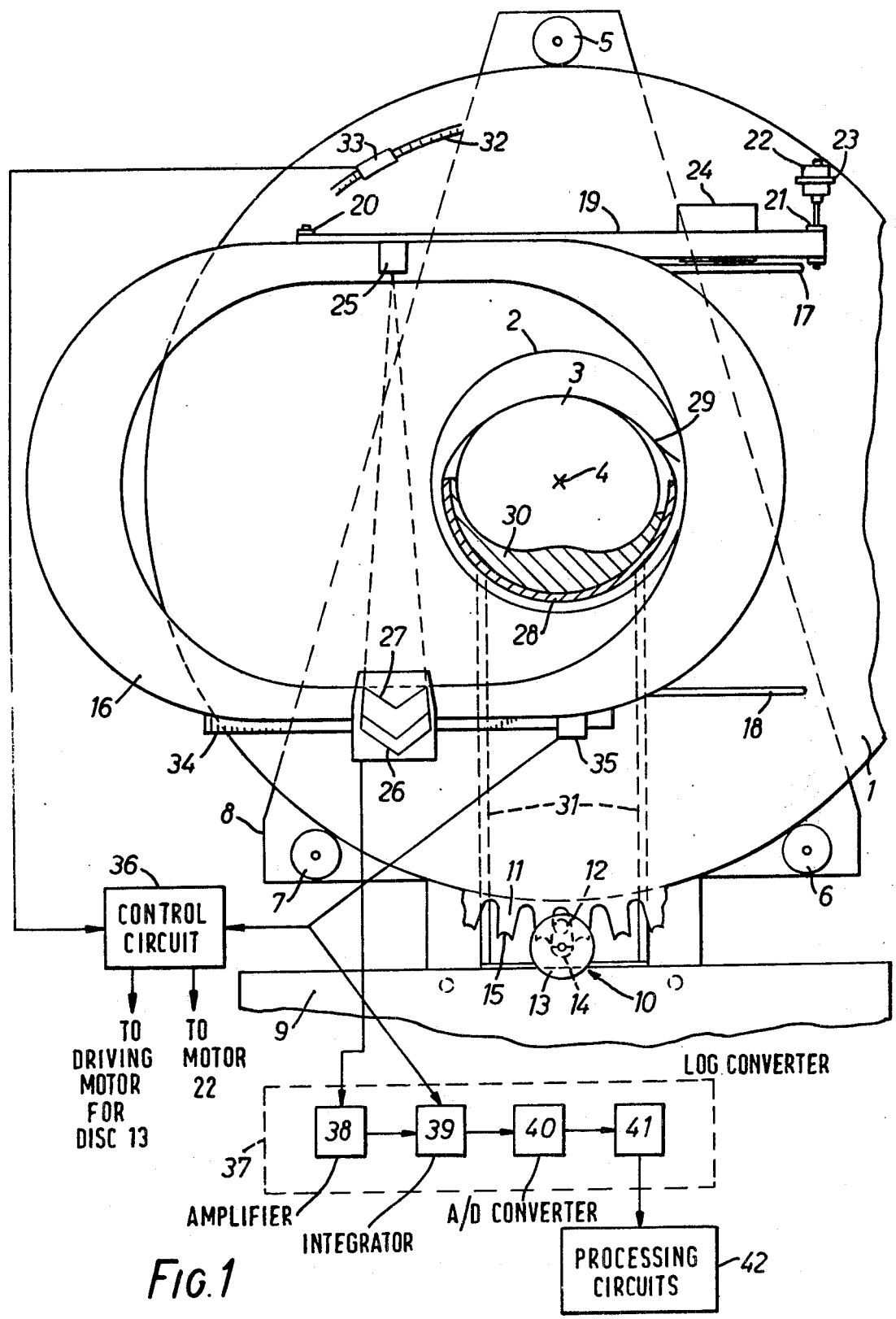

United States Patent [19]

Hounsfield et al.

[11] 4,153,839
[45] May 8, 1979

[54] RADIOGRAPHY

[75] Inventors: Godfrey N. Hounsfield, Newark; Tai Y. Chan, Old Windsor, both of England

[73] Assignee: EMI Limited, Hayes, England

[21] Appl. No.: 823,639

[22] Filed: Aug. 11, 1977

[30] Foreign Application Priority Data

Aug. 28, 1976 [GB] United Kingdom ............... 35911/76

[51] Int. Cl.² ..................... G01T 1/20; G01N 21/34
[52] U.S. Cl. ............................. 250/366; 250/367; 250/445 T
[58] Field of Search ........... 250/361, 366, 367, 445 T, 250/483

[56] References Cited

U.S. PATENT DOCUMENTS

| | | | |
|---|---|---|---|
| 3,720,831 | 3/1973 | Miraldi | 250/366 |
| 4,010,371 | 3/1977 | Le May | 250/366 |
| 4,035,647 | 7/1977 | Hounsfield et al. | 250/366 |

Primary Examiner—Alfred E. Smith
Assistant Examiner—Janice A. Howell
Attorney, Agent, or Firm—Cooper, Dunham, Clark, Griffin & Moran

[57] ABSTRACT

The specification discloses a scintillator crystal configuration which enables a group of crystals to be closely packed together, for example in a V-formation. Each crystal receives x-radiation through an input face, which is of small area, and emits light through an output face, to which a photodiode is preferably attached and which is therefore of larger area than the input face. Also disclosed is a medical radiographic apparatus incorporating an X-ray detector unit containing a number of such crystals.

13 Claims, 6 Drawing Figures

RADIOGRAPHY

The present invention relates to radiography, and it relates especially, though not exclusively, to radiographic apparatus by means of which it is possible to determine the absorption or transmission coefficients at a plurality of locations distributed over a substantially planar slice cross-sectionally disposed in the body of a patient under examination. An apparatus for, and method of, effecting the evaluation referred to above is described and claimed in U.S. Pat. No. 3,778,614.

The technique for such evaluation involves determining the amount of radiation absorbed on traversing each of a large number of linear paths through the patient's body in the plane of the slice and suitably processing the absorption values so determined. In order to project the radiation through the body along all of the aforementioned paths, the source of the radiation and an associated detector means are scanned relative to the body.

The aforementioned Patent Specification discloses techniques for effecting the scanning and the processing; faster scanning techniques are described and claimed in U.S. Pat. No. 3,946,234 and U.S. Pat. No. 4,035,647, whereas a faster processing technique is described and claimed in U.S. Pat. No. 3,924,129.

The processing technique disclosed in the aforementioned U.S. Pat. No. 3,924,129 involves a form of convolution of the determined absorption data in which the data are assembled in sets corresponding to sets of paths through the body and each determined absorption value is modified by being combined with the values relating to other paths of the same set, each weighted in accordance with a weighting function which decreases in amplitude with increasing distance of the path corresponding to the value being weighted from the path corresponding to the value being modified. The modified values are then superimposed in layergram format.

In a typical apparatus such as that described in U.S. Pat. No. 3,946,234 a source of X-radiation provides a planar beam of radiation emanating in a ten degree fan from a substantially point source. On the opposite side of the patient's body an array of thirty collimators divides the fan beam into thirty substantially pencil beams, at $\frac{1}{3}°$ angular spacing in the fan. Each pencil beam is incident on a respective detector which is typically a scintillator crystal to convert the radiation to light. The intensity of the light is then measured by a respective photomultiplier or photodiode.

In order to improve the resolution of such apparatus it is desirable to provide an increased number of pencil beams at a reduced spacing across the fan. In one example ninety beams, at 1/9° spacing, are provided. It has been proposed to achieve closer spacing of detectors by staggering them at different distances from the source of radiation; such a proposal can be found, for example in U.S. Pat. No. 3,973,128. Alternatively it has been proposed, for example in U.S. Pat. No. 3,866,047, to place the scintillator crystals in line but to mount the light detectors on different faces thereof. This, however, can still lead to problems of packing the scintillator crystals which must be sufficiently closely packed to allow the required number an yet provide satisfactory efficiency. Similar problems can also arise with other geometries of apparatus for which the detectors need to be closely packed. It is an object of this invention to provide a solution to that problem.

According to one aspect of the invention there is provided a scintillator crystal, for converting penetrating radiation to electromagnetic radiation, which is substantially of a wavelength in the visible band, for measurement by at least one photosensitive device, said crystal having a plurality of substantially planar surfaces including a first surface for receiving the penetrating radiation and a second surface suitable to permit the electromagnetic radiation to exit therethrough, the arrangement of the said surfaces being such that, for a first surface or a projection thereof on the perpendicular to an input beam of penetrating radiation, of width less than the input surface of said at least one photosensitive device, the second surface is disposed so as to receive light emitted in response to the radiation but is of sufficient width to accommodate the said input surface of said device.

According to a second aspect of the invention there is provided a scintillator crystal having seven faces of which two faces are in parallel planes and the remaining five are in planes substantially perpendicular to said first mentioned planes.

According to a third aspect of the invention there is provided a radiographic apparatus, for examining a body, said apparatus including a source of a substantially planar fan shaped spread of radiation, directed at the body from a substantially point source, collimator means, disposed on the opposite side of the body to the source, arranged to define a plurality of beams of radiation within the said spread, a plurality of scintillator crystals according to one of the two preceding paragraphs and a plurality of photosensitive devices cooperating with the said crystals to provide output signals indicative of the intensity of radiation transmitted through the body along said narrow beams, for processing to provide a distribution of absorption coefficients for said radiation in a region of the body, the arrangement being such that, from a beam disposed substantially at the centre of the fan to one disposed at an extreme thereof, the collimators and respective crystals and photosensitive devices are disposed progressively nearer to the point source.

Figure 3:
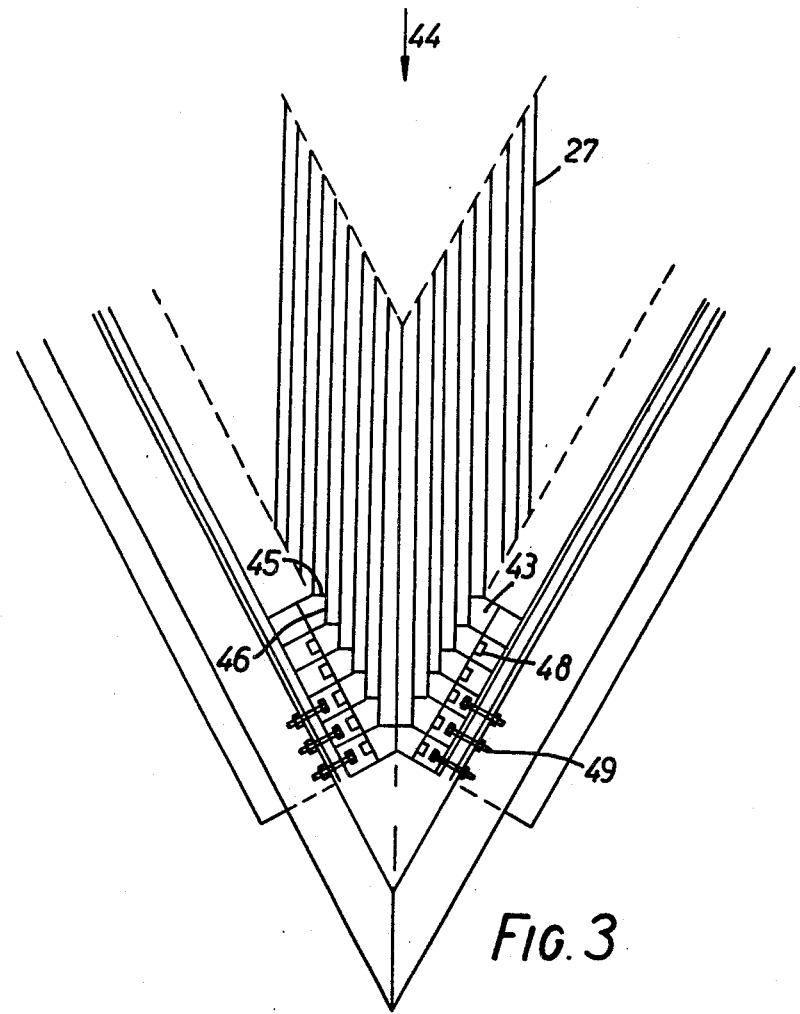
Figure 2A:
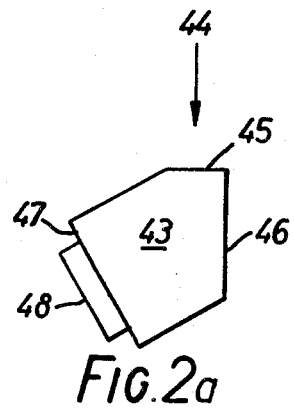
Figure 2B:
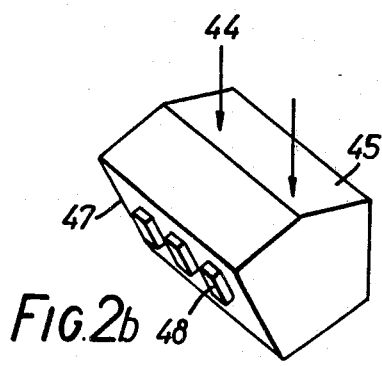
Figure 4:
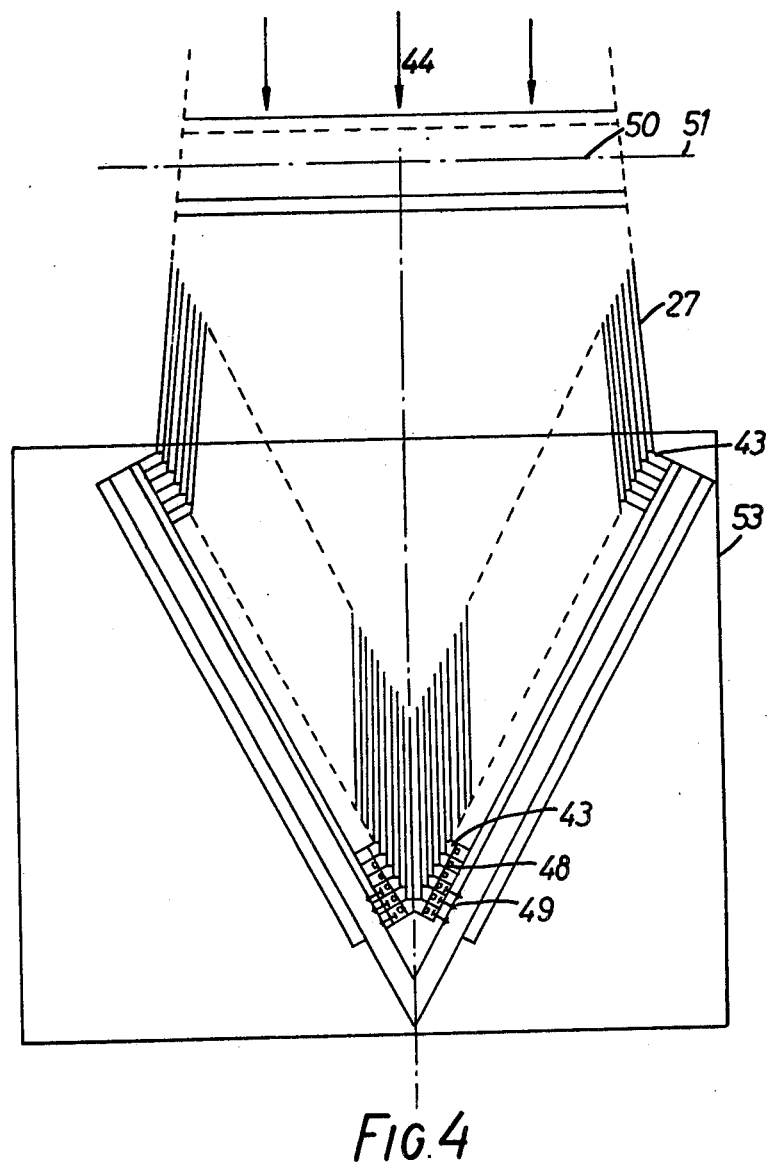
Figure 5:
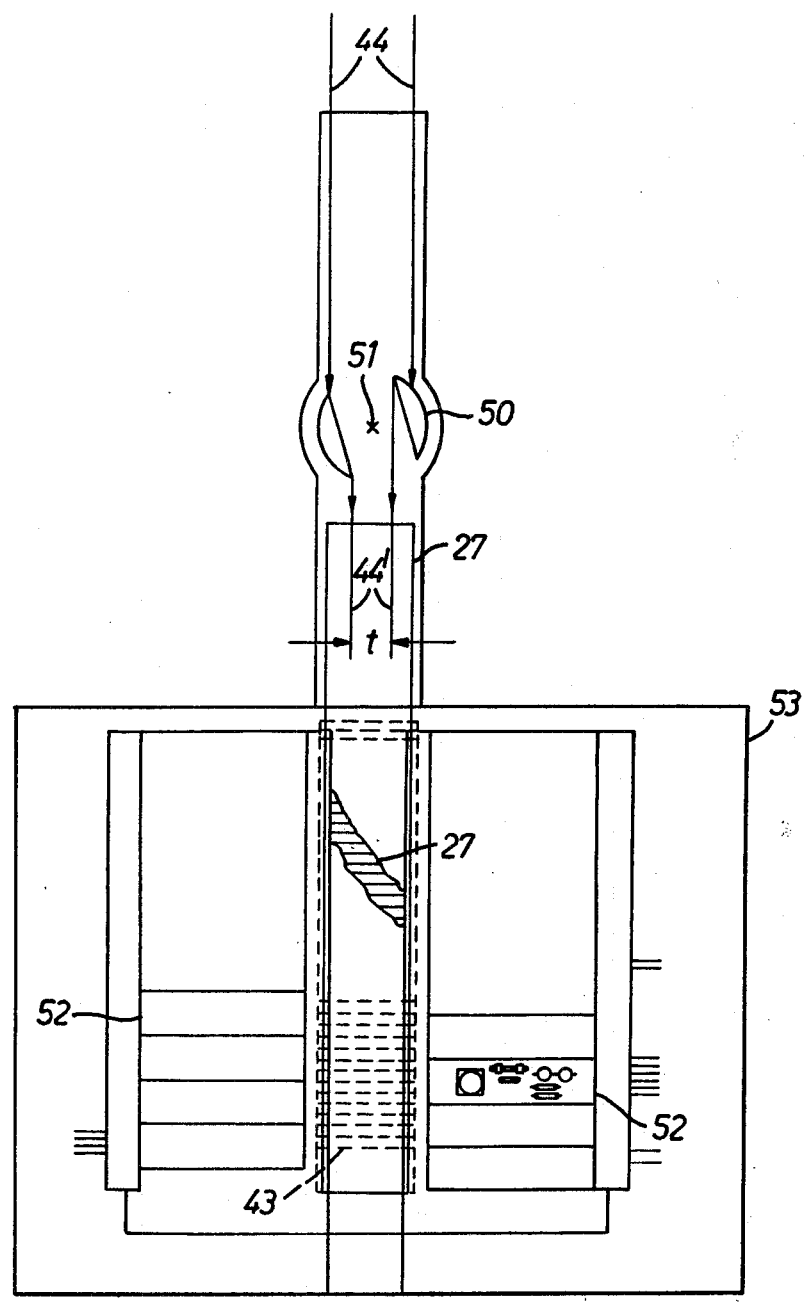

In order that the invention may be clearly understood and readily carried into effect an example thereof will now be described with reference to the accompanying drawing of which, FIG. 1 shows a radiography apparatus incorporating the invention, FIGS. 2a and 2b shows a scintillator crystal in end elevation and perspective views respectively, FIG. 3 illustrates the manner of stacking scintillator crystals in accordance with the invention and FIGS. 4 and 5 show respectively side and end elevations of a complete collimator/detector unit in accordance with the invention.

Referring now to FIG. 1, the apparatus shown therein is similar in principle to the apparatus described in the aforementioned U.S. Pat. No. 3,946,234. A turntable member 1 having a central aperture 2, to accommodate a body 3 to be examined, is mounted vertically for rotation about an axis 4 which is disposed centrally in the aperture 2. The member 1 is supported on three rotary bearings 5, 6 and 7 which are journalled in a main frame 8 for the apparatus. The frame 8 remains stationary, being rigidly secured to a pedestal 9, and can take any suitable form, although it must of course be formed with an aperture coincident with the aperture 2.

The member 1 can be rotated in angular steps of (in this example) ten degrees by means of a Geneva mechanism generally shown at 10. The periphery of member 1 is formed with suitable projections such as 11 which define slots arranged to co-operate with a peg 12 on a continuously rotated disc 13 to effect the required stepwise rotary movement. The disc 13 also carries a locking cam 14 which co-operates with suitable recesses such as 15, on the prongs such as 11, to effectively lock the member 1 in its angular position, so long as the peg 12 is not in one of the slots formed between adjacent prongs 11. Disc 13 is journalled in the main frame 8 and is driven by an electric motor which is not shown.

Mounted upon the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets (not shown) secured to the member 1, and to which belt the yoke 16 is attached by means of a bracket (not shown). The roller 20 is merely an idler roller, but roller 21 is driven by a reciprocating motor 22 which is attached by a strap-like bracket 23 to the member 1.

A counter-balance weight 24 is secured to the opposite run of belt 19 to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped beam emanating from an effective point source. On the opposite side of yoke 16, with respect to the aperture 2, to the source 25 is an array 26 of detectors sensitive to the radiation generated by the source 25, each viewing the source through a respective collimator. In this example ninety collimators are disposed in a bank 27 over a spread of ten degrees, as will be further described hereinafter.

The body 3 is supported on a semi-cylindrical bed 28 and is secured thereon by means of straps such as 29. Gaps between the body and the bed are filled with a suitable packing material 30 which is preferably of dough-like or particulate consistency and absorbs the X-radiation to substantially the same extent as does human tissue. The material 30 is preferably contained in one or more plastic bags. The bed 28 is supported by legs 31 which stand on the pedestal 9.

It will be evident that the stepped, rotational scanning motion imparted by the Geneva mechanism 10 to the member 1 needs to be synchronised with the lateral scanning motion imparted to the yoke 16 by the reciprocating motor 22 and to this end the member 1 is formed with an annular graticule, part of which is shown at 32, and a fixed photodetector 33 is provided, together with a suitable light source (not shown) to provide timing pulses indicative of the passage of markings on the graticule 32 past the photodetector 33. Thus the rotational scanning motion of member 1 can be monitored and similarly linear graticule 34 is fixedly attached to the yoke 16 and co-operates with a second photodetector 35, which is mounted on the member 1 so as to rotate therewith, and a similarly mounted light source (not shown) to produce timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor (not shown) which drives the disc 13 of the Geneva mechanism 10 in such a way that after each step of rotational motion a single lateral scan is carried out to scan the source 25 and the detector array 26 in one direction or the other across the aperture 2. Thus a single lateral scan is carried out for each dwell angle of the member 1, these dwell angles being in this example ten degrees apart.

Each detector in the array 26 comprises a scintillator crystal (in this example calcium iodide doped with thallium) and an associated photodiode, and thus provides electrical signals indicative of the amount of radiation detected thereby. The electrical signals so provided are applied to respective preprocessing circuits 37, each of which contains an amplifier 38, a resettable integrator 39, an analogue-to-digital converter circuit 40 and a logarithmic converter circuit 41. The integrators 39 are read and reset synchronously and periodically by means of timing pulses derived from the photodetector 35; the arrangement being such that the reading and re-setting occurs some one hundred and sixty times during each lateral scan in either direction. Thus, during a single lateral scan, output signals are provided which are indicative of the absorption suffered by the X-radiation on traversing a set of one hundred and sixty parallel paths from the source to the detector at each of ninety angular orientations with respect to the body 3. The member 1 is then rotated through ten degrees and a second group of ninety sets of one hundred and sixty output signals are derived. The process is repeated until the member 1 has been rotated through at least 170°. All of the output signals obtained during the scanning are applied to an input store of a processing circuit 42. The output signals are withdrawn from the store in a suitable sequence and used to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described and claimed in U.S. Pat. No. 3,924,129. As previously mentioned, this technique involves a form of convolution and the output signals are processed in sets relating to sets of paths through the body. Each output signal is modified by combining it with weighted components of other output signals of its own set; the weighting being in accordance with a function which is negative, and decreases in amplitude as the distance from the path giving rise to the output signal being weighted to the path giving rise to the output signal being modified increases. The modified output signals are then additively combined in accordance with the inter-relationship of the paths to which they relate in accordance with a layergramming procedure, the modification of the output signals being such as to compensate for the known inaccuracies of conventional layergrams.

The configuration of the detectors used in this invention will now be considered in greater detail. FIG. 2a shows a single calcium iodide scintillator crystal 43 of a shape which, in accordance with the invention, allows a suitable density of packing. X-rays 44 are intended to be incident on a face 45 which is, in this example, to be perpendicular to the X-rays although this is not necessary. A face 46 is arranged to be substantially parallel to the X-ray direction so as to abut the collimator for the adjacent channel and another face 47 carries one or more photodiodes 48. Face 47 is arranged so that light output of the scintillator can efficiently illuminate the face while keeping the photodiode 48 out of the direct X-ray path and allows a sufficient area for efficient use of the photodiode. Faces other than face 47 can be silvered to prevent excessive loss of light. A crystal is also shown in perspective view in FIG. 2b, with three photodiodes 48 distributed along the length dimension, which corresponds to the thickness of the X-ray slice.

The manner of mounting a plurality of crystals 43 and corresponding detectors 48 is shown in FIG. 3. The collimator 27, made of molybdenum or similar material, are slightly inclined to one another to point at the source 25. Each collimator directs X-rays to a respective crystal 43 and abuts at one end the face 46 of one adjacent crystal. The crystals are mounted with parallel faces in contact so that the photodiodes 48 are in line, the whole stack being in a 'V'-formation. Crystals mounts 49 are illustrated although these may take any form desired to hold the crystals in the required formation.

It will be understood that the significant factors affecting the crystal shape are that the surface 47 should be large enough to hold the photodiodes required and allow packing of adjacent ones thereof, although surface 45 cannot be so large, and that surface 47 should be disposed to allow efficient light collection while preferably keeping the photodiode 48 from direct X-ray illumination through too small a crystal path. Minor variations of the crystal design shown, which still satisfy these conditions, will be apparent to those skilled in the art.

For further understanding of the arrangement in accordance with the invention the full collimator and detector array is illustrated in simplified form in FIGS. 4 and 5 in end and side elevation respectively. Some details of mounting brackets are also shown but will not discussed individually since their exact form is not critical. FIG. 4 shows more clearly the 'V'-shaped configuration of the entire array, which allows the desired packing.

Both FIGS. 4 and 5 show a variable throat arrangement which allows adjustment of the X-ray beam and hence slice thickness dimension t. The thickness of the X-ray slice as defined by the examining X-rays 44, passing through body 3, is set by collimator plates, not shown, at the source 25. It is not desirable to subject the patient to unnecessary X-rays and so removal of excess at the source is preferred. However, a fine adjustment to alter the thickness of the slice of the final picture is provided by two extended 'D'-cross-section members 50 which are arranged to rotate about an axis 51 to restrict the X-rays 44 as shown at 44.

As can also be seen in FIG. 5 amplifiers 52, one for each crystal 48 are mounted on the detector mount in a similar 'V'-formation but on alternate sides to allow a suitable density for the relatively large boards. It should be noted, however, that each photodiode could also be an integrated circuit incorporating a preamplifier. The whole is mounted in a protective casing 53.

It should be noted that other modifications mau be made to the complete radiographic apparatus, as shown in FIG. 1, without departing from the scope of the invention. For example attenuating means may be additionally disposed in the path of the radiation to substantially correct for variations in absorption resulting from different radiation path lengths through the body 3.

Furthermore the invention may be used in other apparatus, for which close packing of detectors required, including apparatus in which a stationary array of detectors partly or wholly surrounds the body and the radiation is scanned relative to them. For use with such an apparatus the detectors would be stacked in a series of V formations, as in FIG. 3, the whole forming an approximate circle.

What we claim is:

1. A scintillator crystal, for converting penetrating radiation to electromagnetic radiation, which is substantially of a wavelength in the visible band, for measurement by at least one photosensitive device, said crystal having a plurality of substantially planar surfaces including a first surface for receiving the penetrating radiation and a second surface suitable to permit the electromagnetic radiation to exit therethrough, the arrangement of the said surfaces being such that, for a first surface or a projection thereof on the perpendicular to an input beam of penetrating radiation, of width less than the input surface of said at least one photosensitive device, the second surface is disposed so as to receive light emitted in response to the radiation but is of sufficient width to accommodate the said input surface of said device.

2. A crystal according to claim 1 in which the first surface is of width less than the said device and the second surface is inclined to the first surface.

3. A crystal according to claim 1 in which surfaces other than one at which penetrating radiation is intended to enter and one at which visible electromagnetic radiation is intended to leave, are silvered to reduce loss of visible radiation.

4. A crystal according to claim 1 having at least one photosensitive device attached to a surface from which visible electromagnetic radiation is intended to leave.

5. A crystal according to claim 4 in which the at least one photosensitive device is at least one photodiode.

6. A crystal according to claim 5 in which the at least one photodiode takes the form of an integrated circuit incorporating an amplifier.

7. In combination a scintillator crystal, for converting penetrating radiation to electromagnetic radiation which is substantially in the visible band, and at least one photosensitive device for measuring the intensity of said visible electromagnetic radiation, said crystal having a plurality of substantially planar surfaces including a first surface for receiving the penetrating radiation of a beam incident thereon and a second surface suitable to permit the visible electromagnetic radiation to exit therethrough, wherein the first surface is of dimension smaller than the total input surface of the at least one photosensitive device and the second surface is of dimension larger than said total input surface.

8. In a radiographic apparatus a plurality of scintillator crystals each for receiving a beam of penetrating radiation for conversion to electromagnetic radiation, which is substantially of a wavelength in the visible band, to be measured by photosensitive devices, wherein each crystal is arranged with an output surface of dimension greater than the cross-section of the respective beam and inclined to the mean direction of said beam to allow close packing of said crystals.

9. A radiographic apparatus, for examining a body, said apparatus including a source of a substantially planar fan-shaped distribution of radiation, directed at the body from a substantially point source, collimator means, disposed on the opposite side of the body to the source, arranged to define a plurality of narrow beams of radiation within the said distribution, a plurality of scintillator crystals and a plurality of photo-sensitive devices cooperating with the said crystals to provide output signals indicative of the intensity of radiation transmitted through the body along said narrow beams, for processing to provide a distribution of absorption coefficients for said radiation in a region of the body, wherein one or more photosensitive devices associated with a crystal have a total input surface of dimension greater than the cross-section of the respective beam perpendicular to its mean direction and each scintillator crystal has a first, input, surface disposed to receive radiation of the respective beam and an output surface disposed to permit electromagnetic radiation, generated in the crystal in response to the radiation of said beam, to exit therefrom and of sufficient dimension to accommodate the total input surface of the one or more photosensitive devices and wherein the arrangement of the crystals is such that, from a beam disposed substantially at the centre of the fan to one disposed at an extreme thereof, the collimators and respective crystals and photosensitive devices are disposed progressively nearer to said source.

10. An apparatus according to claim 9 in which the photosensitive devices are photodiodes.

11. A radiographic apparatus, for examining a body, said apparatus including a source of a substantially planar fan-shaped distribution of radiation, directed at the body from a substantially point source, means for orbiting the source about an axis intersecting the body to direct the radiation through the body from a plurality of mean directions, a plurality of scintillator crystals disposed about the body to receive the radiation after passage therethrough and a plurality of photosensitive devices cooperating with the crystals to provide output signals indicative of the intensity of the radiation transmitted through the body along narrow beams defined within the fan, for each of said mean directions, for processing to provide a distribution of absorption coefficients for said radiation in a region of the body wherein one or more photosensitive devices associated with each crystal have a total input surface of dimensions greater than the cross section of the respective beam perpendicular to its mean direction and the scintillator crystals are each formed with an output surface, suitable to permit electromagnetic radiation generated in the crystal to exit therefrom, of dimensions sufficient to accommodate the total input surface of the respective one or more photosensitive devices and wherein the arrangement is such that the crystals and photosensitive devices are disposed in at least one stack in which successive crystals and devices are progressively nearer to said source.

12. A radiographic apparatus, for examining a region of a body, including a substantially point source of a substantially planar fan-shaped distribution of penetrating radiation, directed at the body, collimator means, disposed on the opposite side of the body to the said source, arranged to define a plurality of beams of radiation within the said distribution, a plurality of scintillator crystals and a plurality of photosensitive devices, the crystals being disposed in at least one stack in the plane of the said distribution such that a first surface of each crystal, or a projection thereof, being of width less than the input surface of a photosensitive device, is substantially perpendicular to the mean direction of a respective beam, and a second surface thereof is at an angle to said mean direction of a respective beam and the second surfaces of a number of crystals are parallel to each other, and the photosensitive devices being arranged with the input surfaces thereof aligned with the second surfaces of respective crystals to measure the intensity of light emanating therefrom, and representing the intensity of radiation transmitted through the body along respective beams, for processing to provide a representation of the distribution of the absorption of the radiation in the said region.

13. A radiographic apparatus, for examining a body, said apparatus including a source of a substantially planar fan-shaped distribution of radiation, directed at the body from a substantially point source, a plurality of scintillator crystals arranged to receive the radiation after passage through the body and a plurality of photosensitive devices, at least one disposed with its input surface aligned with an output surface of each crystal of dimensions sufficient to accommodate said input surface, to cooperate with said crystals to provide output signals indicative of the intensity of radiation transmitted through the body along narrow beams defined within the fan-shaped distribution, for processing to provide a distribution of absorption coefficients for said radiation in a region of the body, the arrangement being such that, the crystals and photo-sensitive devices are disposed in at least one V-shaped stack.

* * * * *